United States Patent [19]

Harris

[11] 4,430,076

[45] Feb. 7, 1984

[54] COMBINED UTERINE INJECTOR AND MANIPULATIVE DEVICE

[76] Inventor: James H. Harris, 364 W. Lilburn Ave., Roseburg, Oreg. 97470

[21] Appl. No.: 345,777

[22] Filed: Feb. 4, 1982

[51] Int. Cl.³ ............................................. A61M 25/00
[52] U.S. Cl. ..................................... 604/96; 128/658; 128/344
[58] Field of Search ................. 604/55, 96–103; 128/344, 654–658

[56] References Cited

U.S. PATENT DOCUMENTS

| | | | |
|---|---|---|---|
| 397,060 | 0/1889 | Knapp | 604/96 |
| 507,573 | 0/1893 | Wetherbee . | |
| 559,620 | 0/1896 | Shearer . | |
| 2,480,041 | 8/1949 | Myller | 128/2 |
| 2,687,131 | 8/1954 | Raiche | 128/349 |
| 3,459,175 | 8/1969 | Miller | 128/344 X |
| 3,721,229 | 3/1973 | Panzer | 128/658 |
| 3,766,920 | 10/1973 | Greene | 128/246 |
| 3,802,418 | 4/1974 | Clayton | 128/2 F |
| 3,812,841 | 5/1974 | Isaacson | 128/1 R |
| 3,833,004 | 9/1974 | Vazquez et al. | 604/100 |
| 3,882,852 | 5/1975 | Sinnreich | 604/96 X |
| 3,896,816 | 7/1975 | Mattler | 128/349 B |
| 3,948,270 | 4/1976 | Hasson | 604/55 |
| 4,089,337 | 5/1978 | Kronner | 604/96 |

FOREIGN PATENT DOCUMENTS 861300 of 1978 Belgium .

*Primary Examiner*—Dalton L. Truluck
*Attorney, Agent, or Firm*—James D. Givnan, Jr.

[57] ABSTRACT

A combination uterine manipulative and injector device having a multi-lumen catheter for uterine insertion having an inflatable member at its insertable end which when inflated seals the lower portion of the uterus to retain fluid or gas injected into the uterine cavity and contributes to attachment of the device to the uterus. A handle in place on the catheter has a fixed stop engageable with the external os of the cervix to limit catheter insertion. The inflatable member is shaped to prevent catheter tip contact with the uterine wall and to urge the stop into biased engagement with the cervix to effect secure attachment of the device to the uterus enabling manual positioning of the uterus by the device for examination purposes.

8 Claims, 6 Drawing Figures

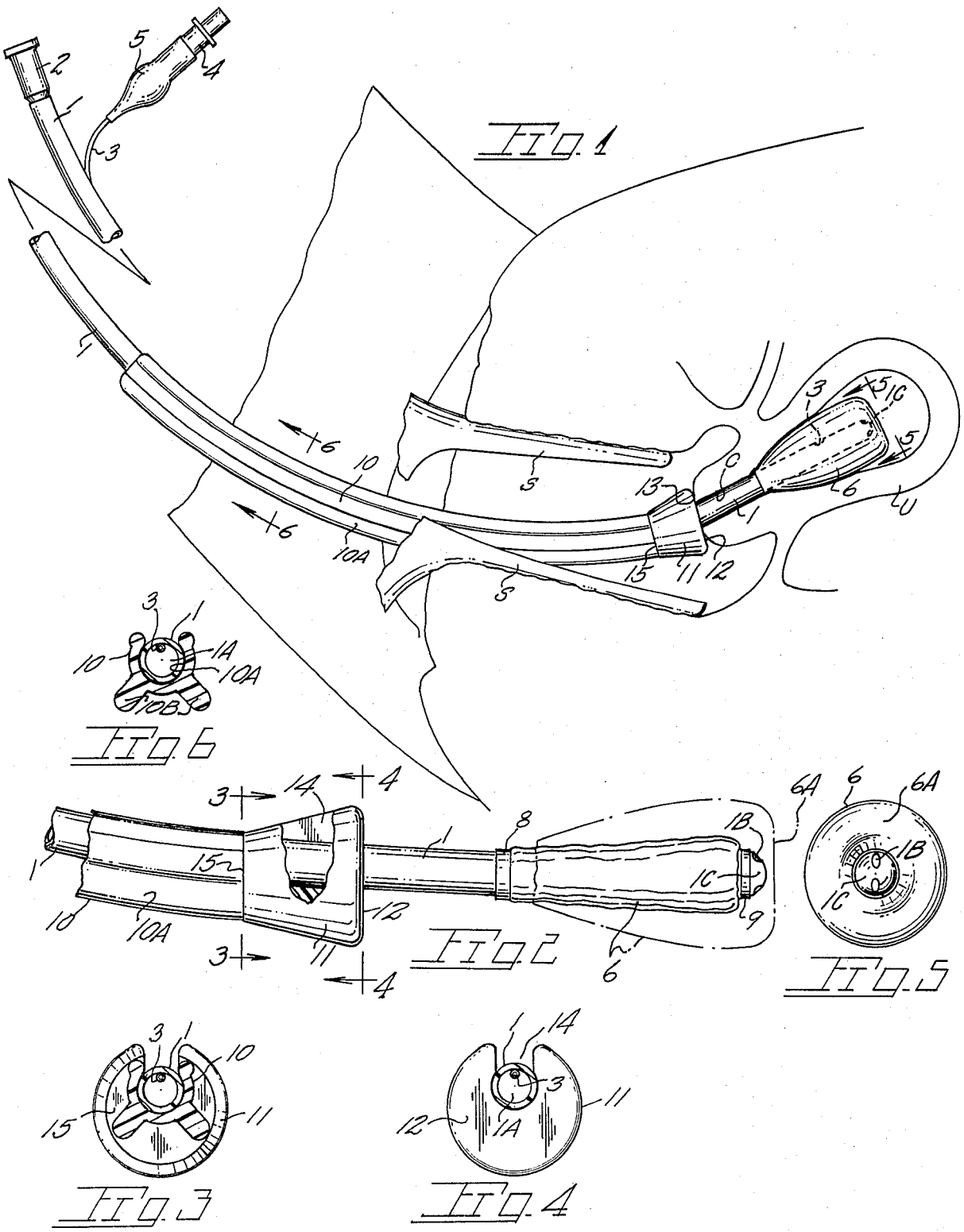

COMBINED UTERINE INJECTOR AND MANIPULATIVE DEVICE

BACKGROUND OF THE INVENTION

The present invention concerns catheters, and particularly a catheter for the injection of fluid into and sealing the uterus with provision made for positioning of the uterus for examination purposes.

Current medical practice includes the injection of gas or fluid into the uterus for better definition of same and the fallopian tubes. The prior art device disclosed in U.S. Pat. No. 4,089,337 is of background interest for the reason that it may function both as an injector and enables both sealing and positioning of the uterus being examined. While the above mentioned device has proved useful some risk exists, if used without care, of contacting the uterine wall with the catheter tip. Further, in certain instances, it may lose its sealing capability.

Other catheter devices, in similarity to the above device, also utilize an inflatable member for effecting a seal within the human body. Such other devices are most commonly directed toward uses other than with the uterus. Examples of such other catheters are found in U.S. Pat. No. 2,687,131; 3,459,175; 3,766,920; 3,802,418; 3,812,841; 3,896,816; 3,948,270. U.S. Pat. No. 507,573 discloses a syringe with a stop thereon limiting syringe insertion. The above disclosures, in some instances, disclose body contacting disks, plates, etc., which limit insertion of a supporting catheter into a body cavity. U.S. Pat. No. 2,687,131 is of interest in that a "pear" shaped inflatable member is disclosed therein which is adapted for external abutment against a body part in a urethral catheter.

The above mentioned device disclosed in U.S. Pat. No. 4,089,337 utilizes a spherical inflatable member from which the catheter tip, when in place, projects toward the upper end of the uterus. Excessive catheter penetration during manipulation of the device could result in tip contact with the uterine wall. Further, the spherical shape of the inflatable member does not conform to the lower portion of the uterus interior and, hence, often forms less than a perfect seal. A spring is relied upon to seat the spherical member against the uterine wall.

SUMMARY OF THE PRESENT INVENTION

The present invention is embodied within a catheter type device having a stop contactible with the external cervical os to position an inflatable member within the uterus to seal off the internal os while simultaneously effecting attachment of the device to the uterus for imparting movement to same.

A curved handle portion of the catheter facilitates both insertion of the catheter into the uterus by making same virtually rigid and, thereafter, the manual positioning of the uterus for various medical procedures such as minilaps, laprascopic tubal occlusion and fertility studies. The curved handle permits insertion of the device with the patient in the dorsorecumbant position simplifying use of the device. An inflation valve permits the remote inflation of the inflatable member or cuff at the inserted end of the catheter which expands into intimate, fluid-tight engagement with the interior of the uterus. Fluid thereafter injected via the catheter into the uterus for examination purposes is prevented from escaping and permits the patient to remain ambulatory during the examination. The inflatable member may be of radio opaque elastic material or filled with an opaque fluid for better definition of the viewed uterine wall when uterine tumors or endometrial cancers are suspected. The catheter's inflatable cuff, in addition to its sealing capability, serves to isolate the catheter tip from injurious contact with the uterine wall. A cervical stop on the catheter limits catheter insertion to additionally assure the avoidance of catheter tip contact with the uterine wall. Accordingly, the uterus is protected from injurious cathteter tip impingement thereagainst during both axial as well as lateral catheter movement during uterus manipulation. The inflatable member at least partially occupies the cervical canal and, upon inflation, biases the catheter inwardly to cause the catheter's cervical stop to seat firmly against the external os with some compression of the cervix to effect a firm connection of the device with the uterus to the extent manipulative forces may be imparted by the device to both large and small uteruses as well as those of an extremely pliable nature for surgical or examination purposes.

Generally speaking, the greater the degree of inflation of the inflatable member the better the seal and the connection formed with the uterus while smaller uteri require less inflation of the inflatable member to effect a secure connection therewith.

Important objectives include the provision of a catheter device enabling the injection of fluid into and sealing of the uterus to facilitate examination of same while simultaneously effecting a gripping action on the pliable uterus to enable manual positioning of the uterus for examination purposes; the provision of a catheter device having a stop thereon contactable with the external cervical os of the uterus to provide a positive limit stop for catheter insertion; the provision of a catheter device having an inflatable member or cuff preferably of gradient shape to seal the uterus to prevent the escape of gas or fluid injected thereinto during uterine examination; the provision of a catheter device wherein an inflatable member is configured so as to isolate the catheter end segment from contact with the uterine wall to avoid risk of injury to same; the provision of a catheter device having an inflatable member into which a radio opaque fluid or gas may be injected for better definition of uterine tumors; the provision of a catheter device having an inflatable member into which liquid or gas radioactive material may be discharged to locate same proximate a uterine tumor.

BRIEF DESCRIPTION OF THE DRAWING

In the accompanying drawing:

FIG. 1 is a sectional view of the lower portion of a human torso with the present device operatively disposed therein and segmented for purposes of illustration;

FIG. 2 is an enlarged fragmentary view of the present device;

FIG. 3 is a vertical sectional view taken along line 3—3 of FIG. 2;

FIG. 4 is a vertical sectional view taken along line 4—4 of FIG. 2;

FIG. 5 is an end elevational view taken along line 5—5 of FIG. 1; and

FIG. 6 is a vertical sectional view taken along line 6—6 of FIG. 1.

DETAILED DESCRIPTION OF THE PREFERRED EMBODIMENT

With continuing attention to the drawing, the reference numeral 1 denotes a flexible catheter which may be of the multiple lumen type equipped with a Luer lock 2 at its distal end to facilitate the injection of fluid into the catheter. A passageway at 1A extends the length of the catheter terminating in openings 1B in a catheter tip 1C for fluid discharge into a body cavity, in this instance, a uterus at U.

A second passageway in the catheter is an air line at 3 which serves to communicate an inflation valve at 4 with the interior of a later described inflatable member. Said valve is of the well known type which admits air from a syringe type pump and automatically seals itself upon extraction of the syringe nozzle. A pilot balloon at 5 provides an inflation indicator for the remotely disposed inflatable member later described.

On the insertable end of the present device is an inflatable member or cuff 6 which in its deflated state lies collapsed about an end segment of the catheter. The end segment terminates at a stop as later described. When inflated, said member assumes a conical shape with an innermost or base end at 6A proximate catheter tip 1C as best viewed in the broken line position in FIG. 2. Cuff ends at 8 and 9 are fixed in an airtight manner to the catheter end segment exterior. As shown in FIGS. 2 and 5, catheter tip 1C does not protrude beyond the inflatable member. Accordingly, the catheter tip is isolated from injurious contact with the endometrium of the uterus. A later described cervical stop additionally serves to minimize the risk of catheter tip contact with to the uterus.

A handle 10 is of elongate, curved configuration with a lengthwise channel 10A therealong to laterally receive the catheter. For retention of the catheter, the lengthwise extending channel is of a cross sectional shape and dimension to firmly engage the catheter exterior whereby axial slippage, intentional or inadvertent of the catheter within said handle is prevented. The handle is preferably curved on a radius of about 13 cm to facilitate catheter insertion into the uterus and subsequent positioning of the uterus by handle manipulation all with the patient in the convenient dorsorecumbant position. Ribs at 10B on the handle serve to reinforce same against bending loads.

At the vaginal or inserted end of handle 10 is a cervical stop 11 embodied in an enlargement having a frontal wall surface 12 contactable with the external os 13 of the cervix. Stop 11 is of truncated conical shape bifurcated at 14 to permit lateral installation of the catheter into the handle and stop during assembly of the device. Stop 11 is of tapered configuration and facilitates withdrawal from the vagina without trauma. Toward the same end, all corners of the stop are radiused. A back wall 15 of the cervical stop is integral with handle 10 and is of lesser size than frontal wall 12. Formation of the stop of a clear plastic permits viewing of the cervix external os therethrough to facilitate catheter insertion. Bifurcating of the stop also contributes to viewing of the external os during insertion.

A satisfactory embodiment of the present device utilizes a catheter 33 cm in length of a semi-rigid material such as of polyvinyl chloride having an outside diameter of 6 mm. Handle 10 may be formed of a rigid plastic such as a vinyl with a length of about 18 cm with stop 11 thereon having a front wall diameter of about 2 cm. Inflatable cuff 6 is preferably of conical shape with an overall length of approximately 4 cm and, when inflated, of a diameter at its largest end or base of about 2 cm. A vaginal speculum at S facilitates insertion of the device into the cervix. The distance from the cervical stop surface 12 to catheter end 1C termed an insertable end segment is approximately 6 to 6.25 cm to avoid risk of uterine wall contact.

With front wall surface 12 of the stop in place against the external os of the cervix, inflatable member 6 is inflated with the earlier mentioned syringe type pump with the inflation of the pilot balloon indicating the remote inflation of member 6 by reason of communicating air line 3. The inflatable member 6 coacts with the somewhat conical lower portion of the uterus to exert an inward axial force on catheter 1 to assure cervical stop 11 at all times being in biased abutment with the external os to exert, along with inflatable member 6, a grasping with some compression of the cervix. At this time, inflatable member 6 is at least partially disposed in the cervical canal at C with the remaining wall surface of the inflatable member at least in partial contact with the lower uterine wall and effect, along with stop 11, secure attachment of the device to the extent subsequent manipulative forces may be imparted to the uterus for examination purposes.

While a conically shaped inflatable member 6 is utilized in the preferred form of the invention, it is to be understood that the inflatable member may be otherwise shaped such as being spherical or ovoid.

While I have shown but one embodiment of the invention it will be apparent to those skilled in the art that the invention may be embodied still otherwise without dparting from the spirit and scope of the invention.

Having thus described the invention, what is desired to be secured under a Letters Patent is:

I claim:

1. A device insertable into the human uterus for examination purposes, said device comprising,
    a catheter having an insertable end segment for passage into the cervical canal and fundus of the uterus,
    an air line substantially coextensive with the catheter and including an air valve,
    an elongate handle fixedly disposed about said catheter and serving to stiffen same,
    a stop in place on one end of said handle and in a fixed relationship with the catheter and contactible during catheter insertion with the external os of the cervix to thereby limit catheter insertion into the uterus, said stop defining one extremity of said catheter insertable end segment,
    said end segment projecting beyond said stop being of a length approximately 6 cm to 6.25 cm to prevent the inserted end of the catheter from forceful contact with the uterine wall, and
    an inflatable member disposed about said end segment of said catheter and in communication with said air line, said inflatable member when inflated being expansible to engage the internal os of the cervix and adjacent uterine wall, said inflatable member upon inflation causing inward biasing of the catheter proportional to the extent of inflation to urge the stop on said handle against the external cervical os to exert a degree of compression on the cervix along with the inflatable member to attach the device in a secure manner to the uterus enabling positioning thereof for examination purposes.

2. The device claimed in claim 1 wherein said inflatable member is disposed about a major portion of said end segment.

3. The device claimed in claim 1 wherein said inflatable member when inflated is of conical shape with an end wall proximate the catheter end to preclude injurious contact of said end with the uterine wall.

4. The device claimed in claim 1 wherein said stop defines an open area to permit viewing of the external os during catheter insertion.

5. The device claimed in claim 4 wherein said handle is of curved configuration and defines a lengthwise extending groove receiving the catheter in a friction tight manner to prevent axial displacement between the catheter and handle, said handle groove in communication with the stop defined open area.

6. The device claimed in claim 1 wherein said stop is of a translucent nature to contribute toward viewing of the external os during catheter insertion.

7. The device claimed in claim 4 wherein said stop is of truncated conical shape with a front sall surface adapted for abutment with the external os of the cervix, said stop being of tapered configuration to prevent trauma during extraction of the device from the body.

8. The device claimed in claim 1 wherein said stop and said inflatable member are at all times in a fixed spaced relationship to each other.

* * * * *